United States Patent [19]

Emonds-Alt et al.

[11] Patent Number: 5,674,881

[45] Date of Patent: Oct. 7, 1997

[54] QUATERNARY AMMONIUM SALTS OF AROMATIC AMINE COMPOUNDS, THEIR PREPARATION AND PHARMACEUTICAL COMPOSITIONS IN WHICH THEY ARE PRESENT

[75] Inventors: Xavier Emonds-Alt, Combaillaux; Vincenzo Proietto, Saint Georges D'Orques; Didier Van Broeck, Murviel Les Montpellier; Jean-Claude Breliere, Montpellier, all of France

[73] Assignee: Elf Sanofi, Paris, France

[21] Appl. No.: 345,341

[22] Filed: Nov. 21, 1994

Related U.S. Application Data

[63] Continuation of Ser. No. 26,154, Mar. 3, 1993, abandoned.

[30] Foreign Application Priority Data

Mar. 3, 1992 [FR] France .................. 92 02542
Oct. 29, 1992 [FR] France .................. 92 12941

[51] Int. Cl.$^6$ .................. A61K 31/445; C07D 409/12; C07D 211/14
[52] U.S. Cl. .................. 514/329; 514/318; 514/321; 514/322; 514/323; 514/326; 514/327; 514/331; 546/193; 546/194; 546/198; 546/199; 546/201; 546/203; 546/205; 546/213; 546/217; 546/224; 546/233
[58] Field of Search .................. 546/193, 194, 546/198, 199, 201, 203, 205, 213, 233, 217, 224; 514/318, 321, 322, 323, 326, 331, 329, 327

[56] References Cited

U.S. PATENT DOCUMENTS 4,916,156  4/1990  Mosse et al. .................. 514/510
5,089,251  2/1992  Mosse et al. .................. 424/47

FOREIGN PATENT DOCUMENTS 0 288 352  10/1988  European Pat. Off. .
0 474 561  3/1991   European Pat. Off. .
0 428 434  5/1991   European Pat. Off. .
0515240    11/1992  European Pat. Off. .

OTHER PUBLICATIONS

Burger "Medicinal Chemistry" Interscience Publisher, p. 42 (1960).
Pine "Organic chemistry" pp. 98–102 1987.

Mountcastle "Medical physiology" 300–303 1968.

"Synthesis and Local Anesthetic Activity of N–Diethylaminoacetyl Derivatives of Naphthylalkylamines", Journal of Medicinal Chemistry, vol. 14, No. 9, 1971, Washington US, pp. 896–897.

"Central Nervous System Activity of Ethyl 1–Naphthylalkylcarbamates", Journal of Medicinal Chemistry, vol. 13, No. 4, 1970, Washington US, pp. 747–748.

"Effects on the Isolated Human Bronchus of SR 48968, a Potent and Selective Nonpeptide Antagonist of the Neurokinin A ($NK_2$) Receptors", Chemical Abstracts, vol. 118, Columbus, Ohio, US:Abstract No. 32786 (1993).

Primary Examiner—Ceila Chang
Attorney, Agent, or Firm—Foley & Lardner

[57] ABSTRACT

The present invention relates to quaternary ammonium salts of the formula

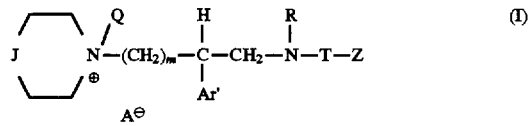

in which:

J is either a group Ar—CXX'—CX" or a group Ar—$(CH_2)_xCH_1$, in which:
Ar is a substituted or unsubstituted phenyl, a cycloalkyl, a pyridyl or a thienyl;
X is hydrogen;
X' is hydrogen or is combined with X" below to form a carbon-carbon bond, or else X and X' together form an oxo group;
X" is hydrogen or forms a carbon-carbon bond with X';
X is zero or one; and
$X_1$ is hydrogen (n=0), a hydroxyl, an alkoxy, an acyloxy, a carboxyl, a carbalkoxy, a cyano or an alkoxyamino group;

Q is an alkyl group or a benzyl group;

A$\ominus$ is an anion;

m is 2 or 3;

Ar', R, T and Z are as defined in the specification, are neurokinin receptor antagonists.

8 Claims, No Drawings

QUATERNARY AMMONIUM SALTS OF AROMATIC AMINE COMPOUNDS, THEIR PREPARATION AND PHARMACEUTICAL COMPOSITIONS IN WHICH THEY ARE PRESENT

This application is a continuation of application Ser. No. 08/026,154, filed Mar. 3, 1993 now abandoned.

The present invention relates to novel quaternary ammonium salts of aromatic derivatives substituted by an amino group and by various ester, amine or amide groups, and to their enantiomers.

The present invention further relates to the method of preparing the compounds and to the use of the compounds according to the invention in compositions for therapeutic use and more particularly in pathological phenomena involving the neurokinin system, such as: pain (D. Regoli et al., Life Sciences, 1987, 40, 109–117), allergy and inflammation (J. E. Morlay et al., Life Sciences, 1987, 41, 527–544), circulatory insufficiency (J. Losay et al., 1977, Substance P, Von Euler, U. S. and Pernow ed., 287–293, Raven Press, New York), gastrointestinal disorders (D. Regoli et al., Trends Pharmacol. Sci., 1985, 6, 481–484) and respiratory disorders (J. Mizrahi et al., Pharmacology, 1982, 25, 39–50).

Ligands endogenous to the neurokinin receptors have been described, such as substance P (SP), neurokinin A (NKA) (S. J. Bailey et al., 1983, Substance P, P. Skrabanck ed., 16–17 Boole Press, Dublin) and neurokinin B (NKB) (S. P. Watson, Life Sciences, 1983, 25, 97–808).

The neurokinin receptors have been recognized on numerous preparations and are currently classed in three types: $NK_1$, $NK_2$ and $NK_3$. Whereas the majority of preparations studied hitherto have several types of receptor, such as guinea-pig ileum ($NK_1$, $NK_2$ and $NK_3$), some of them are said to possess only one type, such as dog carotid artery ($NK_1$), rabbit pulmonary artery devoid of endothelium ($NK_2$) and rat portal vein ($NK_3$) (D. Regoli et al., Trends Pharmacol. Sci., 1988, 38, 1–15).

A more precise characterization of the different receptors is made possible by the recent synthesis of selective agonists. Thus [$Sar^9$, $Met-(O_2)^{11}$]-SP, [$Nle^{10}$]-$NK_{4-10}$ and [$MePhe^7$]-NKB are said to be selective for the $NK_1$, $NK_2$ and $NK_3$ receptors respectively (cf. D. Regoli, 1988 and 1989, op. cit.).

The $NK_2$ receptor and neurokinin A, for example, are involved in neurogenic inflammations of the respiratory tract (P. J. Barnes, Arch. Int. Pharmacodyn., 1990, 303, 67–82, and G. F. Joos et al., Arch. Int. Pharmacodyn., 1990, 303, 132–146).

The patent application EP-A-336230 describes peptide derivatives which are substance P and neurokinin A antagonists and are useful for the treatment and prevention of asthma.

The international patent applications WO 90/05525, WO 90/05729, WO 91/09844 and WO 91/18899 and the European patent applications EP-A-436334, EP-A-429466 and EP-A-430771 describe substance P antagonists.

It has now been found that certain quaternary ammonium salts of aromatic amine compounds possess valuable pharmacological properties as neurokinin receptor antagonists and are useful especially for the treatment of any pathological condition dependent on substance P and neurokinin.

By using a non-peptide substance P antagonist, CP 96,345, Snider et al. (Sciences, 1991, 251, 435–437) have shown that the affinity of such an agonist for the substance P receptors depends very largely on the animal species. Thus, according to these authors, CP 96,345 has a Ki of 240 nM for the rat receptor (3H-SP binding on rat cortical membranes) but a Ki of 3 nM for the bovine receptor (3H-SP binding on bovine caudal membrane). Other authors have shown that CP 96,345 has a Ki of 0.4 nM in substance P binding assays on IM9 and U373 MG human lymphoblastic cells (Gitter et al., Eur. J. Pharmacol., 1991, 197, 237–238).

More particularly, it has been found that certain quaternary ammonium salts, including especially those of the compounds claimed in the patent applications EP-A-428434 and EP 474561, have an increased affinity for the substance P receptors on human cells of the IM9 line.

It has also been found that, totally surprisingly, these quaternary ammonium salts show a considerable increase, compared with the corresponding tertiary amines, in the affinity for the substance P receptors on human cells (IM9) without their affinity for the substance P receptors on rat cortex being substantially reduced.

Finally, contrary to expectation, it has been found that these quaternary salts are active in vivo and by oral administration and that this activity can also be exerted on the central nervous system.

Thus, according to one of its features, the present invention relates to the quaternary ammonium salts of variously substituted aromatic amine compounds of the formula

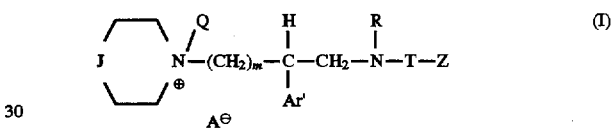

in which:

J is

*—either a group

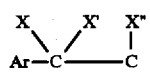

in which:

Ar is a phenyl which is unsubstituted or monosubstituted or polysubstituted by a substituent selected from: hydrogen, a halogen atom, a hydroxyl, a $C_1$–$C_3$-alkoxy, a $C_1$–$C_3$-alkyl and a trifluoromethyl, said substituents being identical or different; a $C_3$–$C_7$-cycloalkyl group; a pyridyl group; or a thienyl group;

X is hydrogen;

X' is hydrogen or is combined with X" below to form a carbon-carbon bond, or else X and X' together form an oxo group; and X" is hydrogen or forms a carbon-carbon bond with X';

*—or a group

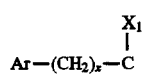

in which:

Ar is as defined above;

x is zero or one; and $X_1$ is hydrogen, only when x is zero; a hydroxyl; a $C_1$–$C_4$-alkoxy; a $C_1$–$C_4$-acyloxy; a carboxyl; a $C_1$–$C_4$-carbalkoxy; a cyano; a group —NH—CO—Alk in which Alk is a $C_1$–$C_6$-alkyl; a mercapto group; or a $C_1$–$C_4$-alkyl-thio group; or else $X_1$ forms a double bond with the carbon atom to which it is bonded and with the adjacent carbon atom in the piperidine;

Q is a $C_1$-$C_6$-alkyl group or a benzyl group;

A⊖ is an anion selected for example from chloride, bromide, iodide, acetate, methanesulfonate and para-toluenesulfonate anions;

m is 2 or 3;

Ar' is a phenyl which is unsubstituted or monosubstituted or polysubstituted by a substituent selected from: hydrogen, a halogen atom, preferably a chlorine or fluorine atom, a trifluoromethyl, a $C_1$-$C_4$-alkoxy and a $C_1$-$C_4$-alkyl, said substituents being identical or different; a thienyl; a benzothienyl; a naphthyl; or an indolyl optionally N-substituted by a $C_1$-$C_4$-alkyl;

R is hydrogen or a $C_1$-$C_6$-alkyl;

T is a group selected from:

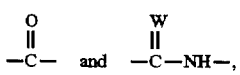

W being an oxygen or sulfur atom; and

Z is hydrogen, M or OM when T is the group

or M when T is the group

M being a $C_1$-$C_6$ alkyl; an α-hydroxybenzyl; an α-hydroxybenzylalkyl or phenylalkyl in which the alkyl is $C_1$-$C_3$ and which is unsubstituted or monosubstituted or polysubstituted on the aromatic ring by a halogen, a trifluoromethyl, a $C_1$-$C_4$-alkyl, a hydroxyl or a $C_1$-$C_4$-alkoxy; a pyridylalkyl in which the alkyl is $C_1$-$C_3$; a naphthylalkyl in which the alkyl is $C_1$-$C_3$ and which is unsubstituted or substituted on the naphthyl ring by a halogen, a trifluoromethyl, a $C_1$-$C_4$-alkyl, a hydroxyl or a $C_1$-$C_4$-alkoxy; a pyridylthioalkyl in which the alkyl is $C_1$-$C_3$; a styryl; or a substituted or unsubstituted mono-, di- or tri-cyclic aromatic or heteroaromatic group.

In the present description, the alkyl groups or the alkoxy groups are linear or branched. The substituents Q are either in the axial position or in the equatorial position.

The tertiary amines which are the precursors of the quaternary amines (I) according to the invention will hereafter be called compounds of formula (Ia):

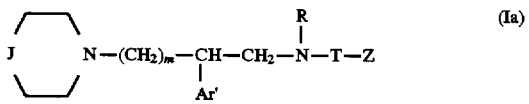

Among these precursors, those of formula (Ia) in which m, Ar', R, T et Z are as defined above and J is a group

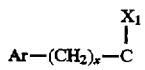

in which Ar is as defined above, x is zero and $X_1$ is hydrogen, and their salts, preferably those which are pharmaceutically acceptable, are novel and form part of the invention.

More particularly, the precursors of formula (Ia'):

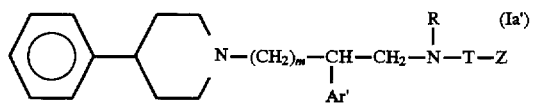

in which m, Ar', R, T and Z are as defined above, and their acid addition salts, preferably those which are pharmaceutically acceptable, are preferred.

Other precursors, namely those of formula (Ia) in which m, Ar', R and J are as defined above, T is —C(O)— and Z is an α-hydroxybenzyl in which the aromatic group is unsubstituted or monosubstituted or polysubstituted by a halogen, a trifluoromethyl, a $C_1$-$C_3$-alkyl, a hydroxyl or a $C_1$-$C_4$-alkoxy, and their salts, preferably those which are pharmaceutically acceptable, are novel and form part of the invention. More particularly, the compounds of formula (Ia"):

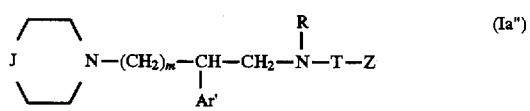

in which J, m, Ar', R, T and Z are as defined above, and their acid addition salts, preferably those which are pharmaceutically acceptable, are more particularly preferred.

The salts of the compounds of formulae (Ia), (Ia') and (Ia") are those formed with mineral or organic acids which permit a suitable separation or crystallization of the compounds of formulae (Ia), (Ia') and (Ia"), such as picric acid or oxalic acid or an optically active acid, for example a mandelic or camphosulfonic acid, or a pharmaceutically acceptable salt such as the hydrochloride, hydrobromide, sulfate, hydrogensulfate, dihydrogenphosphate, methanesulfonate, methylsulfate, maleate, fumarate, naphthalene-2-sulfonate, glycolate, gluconate, citrate or isethionate.

In particular, in formula (I), Z is a mono-, di- or tri-cyclic aromatic or heteroaromatic group which can carry one or more substituents and in which a carbon atom of the aromatic carbocycle or aromatic heterocycle is directly bonded to the group T, or a benzyl group which is unsubstituted or substituted on the aromatic ring by the groups mentioned above for the substituent M=phenylalkyl.

Preferably, Z is an unsubstituted, monosubstituted or polysubstituted phenyl group; an unsubstituted or substituted naphthyl group; or a benzyl group which is unsubstituted or substituted on the aromatic ring by a halogen, a trifluoromethyl, a $C_1$-$C_4$-alkyl, a hydroxyl or a $C_1$-$C_4$-alkoxy.

When Z is a phenyl group, this can preferably be monosubstituted or disubstituted, especially in the 2,4-position but also for example in the 2,3-, 4,5-, 3,4- or 3,5-position; it can also be trisubstituted, especially in the 2,4,6-position but also for example in the 2,3,4-, 2,3,5-, 2,4,5- or 3,4,5-position, tetra-substituted, for example in the 2,3,4,5-position, or pentasubstituted. The substituents of the phenyl group can be: F; Cl; Br; I; CN; OH; $NH_2$; NH—$CONH_2$; $NO_2$; $CONH_2$; $CF_3$; $C_1$-$C_{10}$-alkyl, preferably $C_1$-$C_4$-alkyl, methyl or ethyl being preferred, as well as, for example, n-propyl, isopropyl, n-butyl, isobutyl, sec-butyl, tert-butyl, pentyl or n-pentyl, hexyl or n-hexyl, octyl or n-octyl, nonyl or n-nonyl or decyl or n-decyl; alkenyl containing 2 to 10 carbon atoms, preferably 2-4 carbon atoms, for example vinyl, allyl, prop-1-enyl, isopropenyl, butenyl or but-1-en-1-, -2-, -3- or -4-yl, but-2-en-1-yl, but-2-en-2-yl, pentenyl, hexenyl or decenyl; alkynyl containing 2 to 10 carbon atoms, preferably 2–4 carbon atoms, for example ethynyl, prop-1-yn-1-yl, propargyl, butynyl or but-2-yn-1-yl, pentynyl or decynyl; cycloalkyl containing 3 to 8 carbon atoms, preferably 5 or 6 carbon atoms, cyclopentyl or cyclohexyl being preferred, as well as, for example, cyclopropyl, cyclobutyl, 1-, 2- or 3-methylcyclopentyl, 1-, 2-, 3- or 4-methylcyclohexyl, cycloheptyl or cyclooctyl; bicycloalkyl containing 4 to 11 carbon atoms, preferably 7 carbon atoms, exo- or endo-2-norbornyl being preferred, as well as, for example, 2-isobornyl or 5-camphyl; hydroxyalkyl containing 1 to 5 carbon atoms, preferably 1–2 carbon atoms, hydroxymethyl and 1- or 2-hydroxyethyl being preferred, as well as, for example, 1-hydroxyprop-1-yl, 2-hydroxyprop-1-yl, 3-hydroxyprop-1-yl, 1-hydroxyprop-2-yl, 1-hydroxybut-1-yl or 1-hydroxypent-1-yl; alkoxy containing 1 to 10 carbon atoms, preferably 1–4 carbon atoms, methoxy or ethoxy being preferred, as well as, for example, n-propoxy, isopropoxy, n-butoxy, isobutoxy, sec-butoxy, tert-butoxy, pentoxy, hexyloxy, heptyloxy, octyloxy, nonyloxy or decyloxy; alkoxyalkyl containing 2 to 10 carbon atoms, preferably from 2 to 6 carbon atoms, for example alkoxymethyl or alkoxyethyl, such as methoxymethyl or 1- or 2-methoxyethyl, 1- or 2-n-butoxyethyl or 1- or 2-n-octyloxyethyl; alkoxyalkoxyalkyl containing from 3 to 10 carbon atoms, preferably from 4 to 7 carbon atoms, for example alkoxyalkoxymethyl such as 2-methoxyethoxymethyl, 2-ethoxyethoxymethyl or 2-isopropoxyethoxymethyl, or alkoxyalkoxyethyl such as 2-(2-methoxyethoxy)ethyl or 2-(2-ethoxyethoxy)ethyl; alkoxyalkoxy containing from 2 to 10 carbon atoms, preferably from 3 to 6 carbon atoms, for example 2-methoxyethoxy, 2-ethoxyethoxy or 2-n-butoxyethoxy; alkenyloxy containing 2 to 10 carbon atoms, preferably 2 to 4 carbon atoms, allyloxy being preferred, as well as, for example, vinyloxy, propenyloxy, isopropenyloxy, butenyloxy such as but-1-en-1-, -2-, -3- or -4-yloxy, but-2-en-1-yloxy or but-2-en-2-yloxy, pentenyloxy, hexenyloxy or decenyloxy; alkenyloxyalkyl having 2 to 10 carbon atoms, preferably 3–6 carbon atoms, for example allyloxymethyl; alkynyloxy containing from 2 to 10 carbon atoms, preferably 2 to 4 carbon atoms, propargyloxy being preferred, as well as, for example, ethynyloxy, prop-1-yn-1-yloxy, butynyloxy or but-2-yn-1-yloxy, pentynyloxy or decynyloxy; alkynyloxyalkyl containing from 3 to 10 carbon atoms, preferably 3 to 6 carbon atoms, for example ethynyloxymethyl, propargyloxymethyl or 2-(but-2-yn-1-yloxy)ethyl; cycloalkoxy containing 3 to 8 carbon atoms, preferably 5 or 6 carbon atoms, cyclopentoxy or cyclohexyloxy being preferred, as well as, for example, cyclopropoxy, cyclobutoxy, 1-, 2- or 3-methylcyclopentoxy, 1-, 2-, 3- or 4-methylcyclohexyloxy, cycloheptyloxy or cyclooctyloxy; alkylthio containing from 1 to 10 carbon atoms, preferably 1 to 4 carbon atoms, methylthio or ethylthio being preferred, as well as, for example, n-propylthio, isopropylthio, n-butylthio, isobutylthio, sec-butylthio, tert-butylthio, pentylthio, hexylthio, octylthio, nonylthio or decylthio; alkylthioalkyl containing from 2 to 10 carbon atoms, preferably 2 to 6 carbon atoms, for example methylthiomethyl, 2-methylthioethyl or 2-n-butylthioethyl; acylamino, namely alkanoylamino containing from 1 to 7 carbon atoms, preferably 1 to 4 carbon atoms, formylamino and acetylamino being preferred, as well as propionylamino, butyrylamino, isobutyrylamino, valerylamino, caproylamino or heptanoylamino, or aroylamino or benzylamino; acylaminoalkyl, preferably alkanoylaminoalkyl containing from 2 to 8 carbon atoms, preferably 3 to 6 carbon atoms, such as formylaminoethyl, acetylaminoethyl, propionylaminoethyl, n-butyrylaminoethyl, formylaminopropyl, acetylaminopropyl, propionylaminopropyl, formylaminobutyl or acetylaminobutyl, as well as propionylaminobutyl or butyrylaminobutyl; acyloxy containing from 1 to 6 carbon atoms, preferably 2 to 4 carbon atoms, acetoxy, propionyloxy or butyryloxy being preferred, as well as, for example, formyloxy, valeryloxy or caproyloxy; alkoxycarbonyl containing from 2 to 5 carbon atoms, preferably 2 or 3 carbon atoms, methoxycarbonyl and ethoxycarbonyl being preferred, as well as, for example, n-propoxycarbonyl, isopropoxycarbonyl, n-butoxycarbonyl, isobutoxycarbonyl, sec-butoxycarbonyl or tert-butoxycarbonyl; cycloalkoxycarbonyl containing from 4 to 8 carbon atoms, preferably 6 or 7 carbon atoms, cyclopentoxycarbonyl and cyclohexyloxycarbonyl being preferred, as well as cyclopropoxycarbonyl, cyclobutoxycarbonyl or cycloheptyloxycarbonyl; alkylaminocarbonylamino containing from 2 to 4 carbon atoms, such as methylaminocarbonylamino, ethylaminocarbonylamino or propylaminocarbonylamino; dialkylaminocarbonylamino containing from 3 to 7 carbon atoms, preferably 3 to 5 carbon atoms, dimethylaminocarbonylamino being preferred, as well as di-n-propylaminocarbonylamino or diisopropylaminocarbonylamino; (pyrrolidin-1-yl) carbonylamino; cycloalkylaminocarbonylamino containing from 4 to 8 carbon atoms, preferably 6 or 7 carbon atoms, cyclopentylaminocarbonylamino and cyclohexylaminocarbonylamino being preferred, as well as cyclopropylaminocarbonylamino, cyclobutylaminocarbonylamino or cycloheptylaminocarbonylamino; alkylaminocarbonylaminoalkyl containing from 3 to 9 carbon atoms, preferably 4 to 7 carbon atoms, methylaminocarbonylaminoethyl, ethylaminocarbonylaminoethyl, ethylaminocarbonylaminopropyl and ethylaminocarbonylaminobutyl being preferred, as well as, for example, methylaminocarbonylaminomethyl, n-propylaminocarbonylaminobutyl and n-butylaminocarbonylaminobutyl; dialkylaminocarbonylaminoalkyl containing from 4 to 11 carbon atoms, for example dimethylaminocarbonylaminomethyl, diethylaminocarbonylaminoethyl, diethylaminocarbonylaminopropyl and diethylaminocarbonylaminobutyl; (pyrrolidin-1-yl)carbonylaminoethyl; (piperidin-1-yl) carbonylaminoethyl; cycloalkylaminocarbonylaminoalkyl containing from 5 to 12 carbon atoms, preferably 8 to 11 carbon atoms, cyclopentylaminocarbonylaminoethyl, cyclopentylaminocarbonylaminopropyl, cyclopentylaminocarbonylaminobutyl, cyclohexylaminocarbonylaminoethyl, cyclohexylaminocarbonylaminopropyl and cyclohexylaminocarbonylaminobutyl being preferred, as well as, for example, cyclopropylaminocarbonylaminoethyl or cycloheptylaminocarbonylaminoethyl; alkoxycarbonylaminoalkyl containing from 3 to 12 carbon atoms, preferably 4 to 9 carbon atoms, methoxycarbonylaminoethyl, ethoxycarbonylaminoethyl, n-propoxycarbonylaminoethyl, isopropoxycarbonylaminoethyl, n-butoxycarbonylaminoethyl, isobutoxycarbonylaminoethyl, sec-butoxycarbonylaminoethyl, tert-butoxycarbonylaminoethyl, ethoxycarbonylaminopropyl, n-butoxycarbonylaminopropyl, ethoxycarbonylaminobutyl and n-butoxycarbonylaminobutyl being preferred, as well as, for example, n-propoxycarbonylaminopropyl, n-propoxycarbonylaminobutyl or isopropoxycarbonylaminobutyl; cycloalkoxycarbonylaminoalkyl containing from 5 to 12 carbon atoms, preferably 8 to 11 carbon atoms, cyclopentoxycarbonylaminoethyl, cyclopentoxycarbonylaminopropyl, cyclopentoxycarbonylaminobutyl, cyclohexyloxycarbonylaminoethyl, cyclohexyloxycarbonylaminopropyl and cyclohexyloxycarbonylaminobutyl being preferred, as well as, for example, cyclopropoxycarbonylaminomethyl or cycloheptyloxycarbonylaminoethyl; carbamoylalkyl containing from 2 to 5 carbon atoms, preferably 2 carbon atoms, carbamoylmethyl being preferred, as well as carbamoylethyl, carbamoylpropyl or carbamoylbutyl; alkylaminocarbonylalkyl containing from 3 to 9 carbon atoms, preferably 3 to 6 carbon atoms, methylaminocarbonylethyl, ethylaminocarbonylmethyl, n-propylaminocarbonylmethyl, isopropylaminocarbonylmethyl, n-butylaminocarbonylmethyl, isobutylaminocarbonylmethyl, sec-butylaminocarbonylmethyl and tert-butylaminocarbonylmethyl being preferred, as well as, for example, ethylaminocarbonylethyl, ethylaminocarbonylpropyl, ethylaminocarbonylbutyl, n-propylaminocarbonylbutyl or n-butylaminocarbonylbutyl; dialkylaminocarbonylalkyl containing from 4 to 11 carbon atoms, preferably 4 to 8 carbon atoms, dimethylaminocarbonylmethyl, diethylaminocarbonylmethyl and di-n-propylaminocarbonylmethyl being preferred, as well as, for example, diethylaminocarbonylethyl, diethylaminocarbonylpropyl or diethylaminocarbonylbutyl; (pyrrolidin-1-yl)carbonylmethyl; (piperidin-1-yl) carbonylmethyl; (piperidin-1-yl)carbonylethyl; cycloalkylaminocarbonylalkyl containing from 5 to 12 carbon atoms, preferably 7 or 8 carbon atoms, cyclopentylaminocarbonylmethyl and cyclohexylaminocarbonylmethyl being preferred, as well as, for example, cyclopropylaminocarbonylmethyl, cyclobutylaminocarbonylmethyl, cycloheptylaminocarbonylmethyl, cyclohexylaminocarbonylethyl, cyclohexylaminocarbonylpropyl or cyclohexylaminocarbonylbutyl; alkylaminocarbonylalkoxy containing from 3 to 10 carbon atoms, preferably 3 to 5 carbon atoms, methylaminocarbonylmethoxy being preferred, as well as, for example, methylaminocarbonylethoxy or methylaminocarbonylpropoxy; dialkylaminocarbonylalkoxy containing from 4 to 10 carbon atoms, preferably 4 to 7 carbon atoms, such as dimethylaminocarbonylmethoxy or diethylaminocarbonylethoxy; (piperidin-1-yl)carbonylmethoxy; and cycloalkylaminocarbonylalkoxy containing from 5 to 11 carbon atoms, preferably 7 or 8 carbon atoms, such as cyclopentylaminocarbonylmethoxy or cyclohexylaminocarbonylmethoxy.

The radical Z can also be a pyridyl, thiadiazolyl, indolyl, indazolyl, imidazolyl, benzimidazolyl, quinolyl, benzotriazolyl, benzofuranyl, benzothienyl, benzothiazolyl, benzisothiazolyl, isoquinolyl, benzoxazolyl, benzisoxazolyl, benzoxazinyl, benzodioxinyl or pyridinyl, isoxazolyl, benzopyranyl, thiazolyl, thienyl, furyl, pyranyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromanyl, chromanyl or carbaryl group in which one or more double bonds can be hydrogenated, it being possible for said groups to be unsubstituted or optionally to contain one or more substituents such as: alkyl, phenyl, cyano, hydroxyalkyl, hydroxyl, alkylcarbonylamino, alkoxycarbonyl and thioalkyl groups in which the alkyls are $C_1$–$C_4$.

In formula (I), T is preferably a carbonyl group.

The substituent Ar' is preferably a phenyl group which is advantageously substituted by two chlorine atoms, more particularly in the 3- and 4-positions.

In the same formula (I), m is preferably 2.

The substituent J of formula (I) is advantageously a group

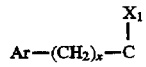

in which Ar is phenyl, x is zero and $X_1$ is hydrogen or an acetylamino group. In advantageous compounds, Z is naphthyl, benzyl or phenyl which are unsubstituted or substituted in the aromatic ring by a substituent selected from chlorine or fluorine and $C_1$–$C_4$-alkyl or -alkoxy. Preferably, Z is a benzyl group substituted by an isopropoxy group, advantageously in the 3-position, or a naphth-1-yl group substituted by a halogen atom, advantageously by a fluorine in the 4-position. More particularly in these advantageous compounds, the group T is a carbonyl, the group R is hydrogen or a methyl group and Ar' is 3,4-dichlorophenyl.

Particularly preferred quaternary compounds according to the present invention are those of formula (I) in which simultaneously:

Z is a 3-isopropoxybenzyl or 4-fluoronaphth-1-yl group;

T is a carbonyl group;

R and Q are both methyl;

Ar' is 3,4-dichlorophenyl;

m is 2; and

A⊖ is a pharmaceutically acceptable anion, chloride or methanesulfonate being particularly preferred.

Among these products, those of the formula

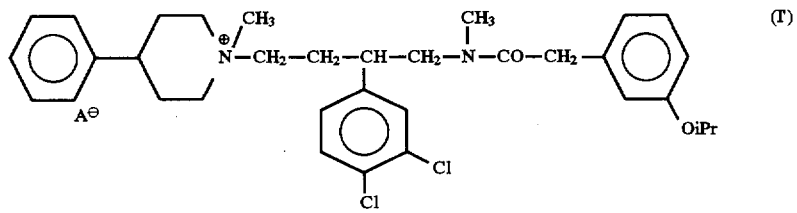

The radical Z can also be a bicyclic aromatic group. When Z is a group such as naphth-1- or -2-yl, said groups can be unsubstituted or can optionally contain one or more substituents selected from: halogens and alkyl, phenyl, cyano, hydroxyalkyl, hydroxyl, oxo, alkylcarbonylamino, alkoxycarbonyl and thioalkyl groups in which the alkyls are $C_1$–$C_4$.

in which iPr is isopropyl and A⊖ is as defined above, especially the methanesulfonate, iodide or chloride ion, are potent substance P antagonists, the compound having the methyl group in the axial position being particularly preferred.

Other compounds of the formula

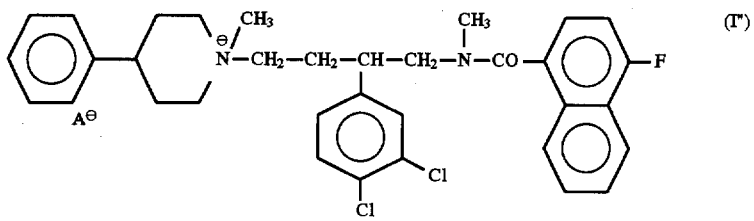 (I")

in which A⊖ is a pharmaceutically acceptable anion, especially methanesulfonate, iodide and chloride, are extremely valuable.

The compounds of formulae (I') and (I") are extremely potent and show a high affinity for the neurokinin-2 and/or -1 receptors. They therefore constitute the preferred feature of the present invention.

N-Methyl-N-[4-(4-phenylpiperidin-1-yl)-2-(3,4-dichlorophenyl)butyl]-3-isopropoxyphenylacetamide of the formula

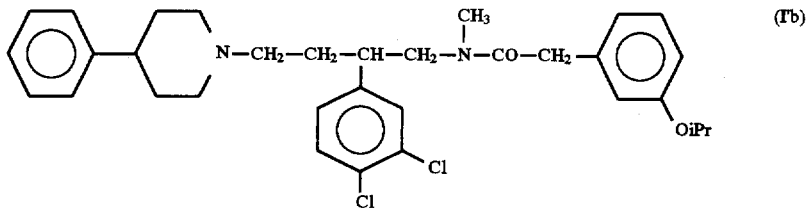 (I'b)

is a key intermediate for the preparation of the compound (I') and itself possesses a very high affinity for the neurokinin receptors. This compound, its enantiomers and its acid addition salts, of which the pharmaceutically acceptable acid addition salts are particularly advantageous, constitute another preferred feature of the present invention.

According to another feature, the present invention relates to a method of preparing the compounds of formula (I), which comprises treating a compound of formula (Ia), in which the amine group which may be present on the substituent Z is N-protected by a customary N-protecting group, in the form of its free base, with an excess of an alkylating agent of the formula

A—Q in which A is a group capable of forming an anion and is as defined above for (I), preferably a chloride or an iodide, and Q is as defined above for (I), and heating the reaction mixture in an organic solvent selected for example from methylene chloride, chloroform, acetone or acetonitrile, at a temperature between room temperature and the reflux point, for one to several hours, to give, after treatment by the customary methods and after deprotection if appropriate, a mixture of the axial and equatorial conformers of the quaternary ammonium salts.

In the case where A⊖ is a pharmacologically unacceptable anion or if in any case it is desired to obtain an anion other than that obtained at the end of the quaternization reaction, this anion can be exchanged with another anion, for example a chloride, by reaction with the appropriate acid, optionally by elution of the compound (I) on an ion exchange resin such as the resin Amberlite IRA68® or Duolite A375®.

The conformers are separated by the customary methods, for example by chromatography or recrystallization.

Each of the axial or equatorial conformers of the compounds (I), in the form of racemates or in the form of optically pure R or S enantiomers, forms part of the invention.

The compounds (Ia) are prepared by a method in which:

a) a free amine of the formula

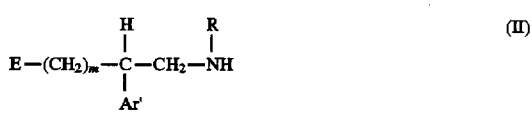 (II)

in which m, Ar' and R are as defined above and E is an O-protected group such as, for example, tetrahydropyran-2-yloxy, or a group

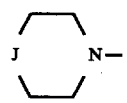

in which J is as defined above, it being understood that: when J is the group

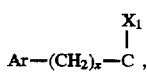

in which $X_1$ is a hydroxyl, this hydroxyl is protected, is treated either with a functional derivative of an acid of the formula

HO—CO—Z (III)

in which Z is as defined above, it being understood that when the group Z contains a hydroxyl, this hydroxyl is protected, when a compound of formula (Ia) in which T is —CO— is to be prepared, or with an iso(thio)cyanate of the formula

W=C=N—Z (III')

in which W and Z are as defined above, when a compound of formula (Ia) in which T is —C(W)—NH— is to be prepared, to give the compound of the formula

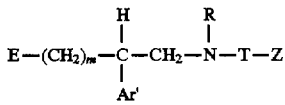 (IV)

b) then, when E is tetrahydropyran-2-yloxy, the tetrahydropyran-2-yl group is removed by reaction with an acid;

c) the resulting N-substituted alkanolamine of the formula

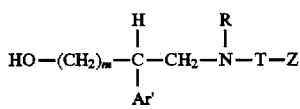 (V)

is treated with methanesulfonyl chloride;

d) the resulting mesylate of the formula

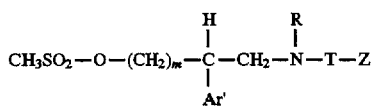 (VI)

is reacted with a secondary amine of the formula

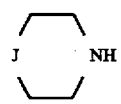 (VII)

in which J is as defined above; and e) after deprotection of the hydroxyl represented by $X_1$, if appropriate, the resulting product is converted, if desired, to one of its pharmaceutically acceptable salts.

To prepare the novel compounds of formula (Ia) in which J is a group

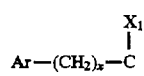

in which Ar is as defined above, x is zero and $X_1$ is hydrogen, the compound (VI) is reacted in step (d) with a 4-Ar-piperidine (Ar being as defined above).

More particularly, to prepare the preferred compounds of formula (Ia'), the mesylate of formula (VI) is reacted with 4-phenylpiperidine (formula VII, J=benzylidene), which is well known in the literature.

The functional derivative of the acid (III) used is either the acid itself, suitably activated for example by cyclohexylcarbodiimide or by benzotriazolyl-N-oxytrisdimethylaminophosphonium hexafluorophosphonate (BOP), or else one of the functional derivatives which react with amines, for example an anhydride, a mixed anhydride, the acid chloride or an activated ester. When Z is a group OM, the acid in question is carbonic acid and the functional derivative used is the monochloride, namely a chloroformate Cl—CO—OM.

When the starting material used is a compound of formula (II) in which E is a group

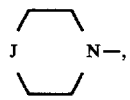

the method of preparing the compounds (Ia) can be represented and illustrated in detail by scheme 1 below:

SCHEME 1

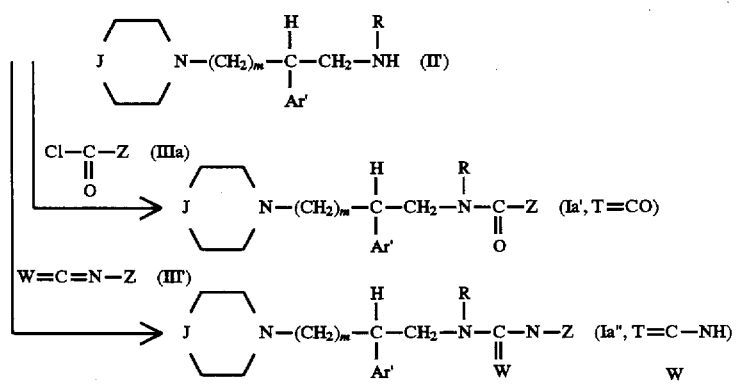

In formula (IIIa) above, the acid chloride is considered as a reactive functional derivative of the acid (III). It is possible, however, to use a different functional derivative or to start from the free acid (III), the procedure being to couple (II') with BOP and then to add the acid (III) in the presence of an organic base such as, for example, triethylamine, in a solvent such as methylene chloride or dimethylformamide, at room temperature; the compounds (I'a) obtained are isolated and purified by the customary methods such as, for example, chromatography or recrystallization.

It is also possible to react (II') with an iso(thio)cyanate W=C=N—Z (III') in an anhydrous inert solvent such as, for example, benzene, overnight at room temperature, and then to treat the reaction mixture by the customary methods to give the compounds (Ia").

When the starting material used is a compound of formula (II) in which E is a tetrahydropyran-2-yloxy group, the method of the present invention can be represented and illustrated by scheme 2.

The reactions of the compound (II") with the reactants (IIIa) and (III') take place as described above for scheme 1, it being possible for the acid chloride (IIIa) to be replaced with a different functional derivative or with the free acid activated for example by BOP.

The intermediate (IV') obtained in this way is deprotected by mild acid hydrolysis to give the free hydroxylated compound (V), from which the mesylate (VI) is prepared in order to substitute it with a secondary amine of formula (VII), finally giving the compounds (Ia).

When the reaction is complete, the compounds of formula (Ia) or, more particularly, of formula (Ia')can be isolated in the form of one of their salts, for example the hydrochloride or oxalate. The free base can be prepared by neutralization of said salt with a mineral or organic base such as sodium hydroxide or triethylamine, or with an alkali metal carbonate or bicarbonate such as sodium or potassium carbonate or bicarbonate.

Resolution of the racemic mixtures (Ia) or, more particularly,(Ia') enables the enantiomers to be isolated.

It is also possible to resolve racemic mixtures of the products of formula (II), especially the products of formulae (II") and (II''') or precursors thereof, in order to prepare the enantiomers of the products of formula (Ia) or, more particularly, of formula (Ia').

The starting compounds of formula (II) are prepared from nitriles of the formula

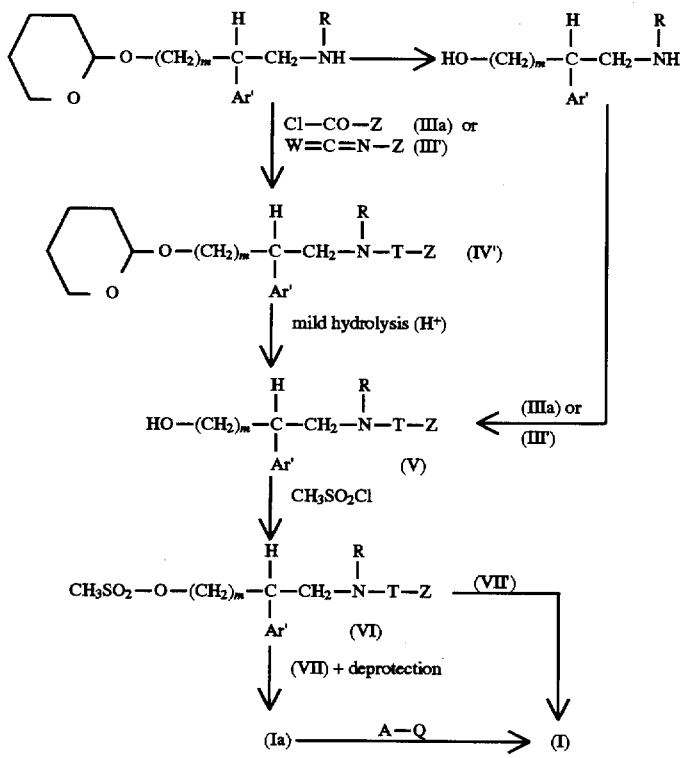

The products of formula (Ia) obtained in this way are isolated, in the form of the free base or a salt, by the conventional techniques.

When the compound of formula (Ia) is obtained in the form of the free base, it can be purified or crystallized by salification by means of treatment with an acid in an organic solvent. Thus treatment of the free base, dissolved for example in an alcohol such as isopropanol, with a solution of the chosen acid in the same solvent gives the corresponding salt, which is isolated by the conventional techniques. The hydrochloride, hydrobromide, sulfate, hydrogensulfate, dihydrogenphosphate, methanesulfonate, methylsulfate, oxalate, maleate, fumarate and naphthalene-2-sulfonate, for example, are prepared in this way.

in which m, E and Ar' are as defined above, by reduction of the nitrile.

To prepare the compounds of formula (II) in which R is hydrogen, the starting nitriles of formula (VIII) are hydrogenated in an alkanol such as ethanol, in the presence of a catalyst such as Raney nickel, and the free primary amine can be isolated by the conventional methods.

When it is desired to prepare the compounds of formula (II) in which R is the methyl group, the free amine, obtained by hydrogenation of the nitrile (VIII) as described above, is treated with a chloroformate, for example with the chloroformate of the formula Cl—CO—OR$_1$, in which R$_1$ is a C$_1$–C$_6$-alkyl, to give the carbamates of the formula

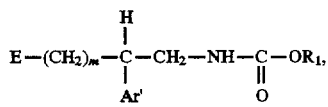

which are then reduced by known means such as reaction with a reducing agent like, for example, a metal hydride such as sodium aluminum hydride or lithium aluminum hydride, or with a boron hydride such as borane dimethylsulfide. The reduction is carried out in a solvent such as ether, toluene or tetrahydrofuran, at a temperature between room temperature and 60° C. The resulting amine of the formula

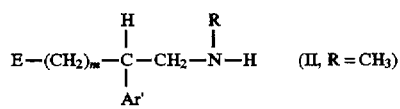

is isolated by the customary methods.

It is also possible to treat the compound of the formula

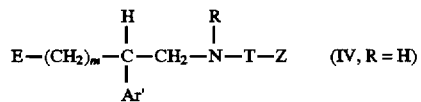

in which m, E, Ar', T and Z are as defined above, with an alkyl halide in the presence of a strong base such as, for example, a metal hydride like, for example, sodium hydride, in an inert solvent such as tetrahydrofuran heated to the reflux point, in order to prepare the compounds (IV) in which R is other than hydrogen.

The nitriles of formula (VIII) are prepared from nitriles of the formula

 (XI)

which, on alkylation with a compound of the formula

 (XII)

in which m and E are as defined above and G is a halogen atom, for example a bromine atom, or a protected hydroxyl group, give the desired compounds (VIII).

The nitriles of formula (VIII) in which E is a tetrahydropyran-2-yloxy group are synthesized from a tetrahydropyran-2-yloxy (THP-O—) derivative obtained by reaction of an alkanol of the formula Br—(CH$_2$)$_m$—OH, in which m is as defined above, with dihydropyran to give the compound

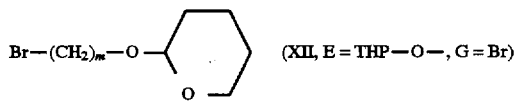

which is then added, in the presence of an alkali metal hydride, to the acetonitrile derivative (XI) in order to prepare the intermediate of the formula

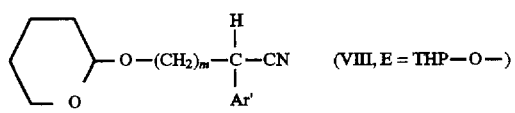

The nitriles of formula (VIII) in which E is a group

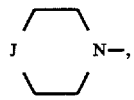

in which J is as defined above, are synthesized by known methods wherein a nitrile derivative of the formula

is added to chlorinated derivatives of the formula

in the presence of sodium amide, in a solvent such as toluene, at temperatures of between 30° and 80° C.

The chlorinated derivative (XIII) is prepared by reaction of a chlorinating reagent such as thionyl chloride with the hydroxylated derivative of the formula

which is itself prepared from the amine of the formula (VII):

in which, if X$_1$=OH, the hydroxyl group is optionally protected by an O-protecting group by the customary methods, with which amine ethylene oxide is reacted if m=2 and a 3-halogenopropanol is reacted if m=3.

An alternative to the preparation of the compounds (I) according to the invention consists in reacting a tertiary amine of the formula

in which J and Q are as defined above for (I), with the methanesulfonate compound (VI) to give directly the quaternary ammonium compound (I) in which A⊖ is represented by the methanesulfonate anion. This reaction is carried out by the customary methods well known to those skilled in the art. The methanesulfonate anion obtained in this way is then optionally exchanged with another anion selected from A⊖ as defined above, for example the chloride anion, using an ion exchange resin as indicated above.

The amines of formulae (VII) and (VII') are known in the literature. A method of preparing them is described in the patent GB 1060160.

The compounds according to the invention were subjected to biochemical and pharmacological tests.

Thus the compounds according to the invention antagonize the binding of substance P to its receptor with a Ki of between 0.1 and 800 nM in tests performed on rat cortex and with a Ki of between 0.01 and 30 nM in tests performed on the lymphoblastic cell line IM9.

The compounds of the present invention have a low toxicity; in particular, their acute toxicity is compatible with their use as drugs. For such a use, an effective amount of a compound of formula (I) is administered to mammals.

The compounds of the present invention are generally administered in dosage units. Said dosage units are preferably formulated as pharmaceutical compositions in which the active principle is mixed with a pharmaceutical excipient.

Thus, according to another feature, the present invention relates to pharmaceutical compositions containing a compound of formula (I) as the active principle.

The compounds of formula (I) above can be used in daily doses of 0.01 to 100 mg per kilogram of body weight of the mammal to be treated, preferably in daily doses of 0.1 to 50 mg/kg. In humans the dose can preferably vary from 0.5 to 4000 mg per day, more particularly from 2.5 to 1000 mg, depending on the age of the subject to be treated or the type of treatment: prophylactic or curative.

In the pharmaceutical compositions of the present invention for oral, sublingual, subcutaneous, intramuscular, intravenous, transdermal, topical or rectal administration, the active principles can be administered to animals and humans in unit forms of administration, mixed with conventional pharmaceutical carriers. The appropriate unit forms of administration include oral forms such as tablets, gelatin capsules, powders, granules and solutions or suspensions to be taken orally, sublingual and buccal forms of administration, subcutaneous, intramuscular, intravenous, intranasal or intraocular forms of administration and rectal forms of administration.

When a solid composition in the form of tablets is prepared, the active principle is mixed with a pharmaceutical vehicle such as gelatin, starch, lactose, magnesium stearate, talc, gum arabic or the like. The tablets can be coated with sucrose or other appropriate substances or they can be treated so as to have a sustained or delayed activity and so as to release a predetermined amount of active principle continuously.

A preparation in the form of gelatin capsules is obtained by mixing the active principle with a diluent and pouring the mixture obtained into soft or hard gelatin capsules.

A preparation in the form of a syrup or elixir can contain the active principle together with a sweetener, which is preferably calorie-free, methylparaben and propylparaben as antiseptics, a flavoring and an appropriate color.

The water-dispersible granules or powders can contain the active principle mixed with dispersants or wetting agents, or suspending agents such as polyvinylpyrrolidone, as well as with sweeteners or taste correctors.

For rectal administration, suppositories are used which are prepared with binders melting at the rectal temperature, for example cacao butter or polyethylene glycols.

For parenteral, intranasal or intraocular administration, aqueous suspensions, isotonic saline solutions or sterile and injectable solutions are used which contain pharmacologically compatible dispersants and/or wetting agents, for example propylene glycol.

For administration by inhalation, an aerosol is used which contains for example sorbitan trioleate or oleic acid, as well as trichlorofluoromethane, dichlorofluoromethane, dichlorotetrafluoroethane or any other biologically compatible propellant gas.

The active principle can also be formulated as microcapsules, with one or more carriers or additives if appropriate.

The active principle can also be presented in the form of a complex with a cyclodextrin, for example α-, β- or γ-cyclodextrin, 2-hydroxypropyl-β-cyclodextrin or methyl-β-cyclodextrin.

The above-mentioned compositions can also contain other active products such as, for example, bronchodilators, antitussives or antihistamines.

In each dosage unit, the active principle of formula (I) is present in the amounts appropriate to the daily doses envisaged. In general, each dosage unit is suitably adjusted according to the dosage and the intended type of administration, for example tablets, gelatin capsules and the like, sachets, ampoules, syrups and the like, and drops, so that such a dosage unit contains from 0.5 to 1000 mg of active principle, preferably from 2.5 to 250 mg, to be administered one to four times per day.

According to another feature, the present invention relates to the use of the products of formula (I) for the preparation of drugs intended for the treatment of physiological disorders associated with an excess of tachykinins, especially substance P, examples being more particularly disorders of the central nervous system, neurodegenerative diseases, respiratory disorders, inflammatory diseases, disorders of the gastrointestinal system, circulatory disorders, pain and migraine. The present invention also includes a method of treating said complaints at the doses indicated above.

The intermediate compounds of formula (Ia) are prepared by the method given in the present description and according to the patent applications EP-A-428434 and EP-A-0474561. Protection of the synthesis intermediates containing amine functional groups is effected by the known methods, for example according to EP-A-512901.

The optically pure compounds (Ia) are also obtained by the method described in the patent applications EP-A-428434 and EP-A-0474561.

The compounds of formula (Ia) in which J is

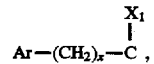

in which Ar is as defined above, x is zero and $X_1$ is hydrogen, especially the compounds of formula (Ia'), are themselves also powerful substance P antagonists, more particularly the compound (I'b), whose Ki is between 0.3 and 0.6 nM in tests performed respectively on rat cortex and on the lymphoblastic cell line IM9.

The $^1H$ nuclear magnetic resonance spectra were run at 200 MHz. The $^{13}C$ nuclear magnetic resonance spectra were run at 50 MHz. The chemical shifts are expressed in ppm.

The melting points, m.p., were measured on a Koffler heating bench.

(a) or (e) denotes the axial or equatorial position of the substituent Q.

The following Examples illustrate the invention without however implying a limitation.

PREPARATIONS

A. AMINOALCOHOLS

PREPARATION I (a) α-(2-Tetrahydropyranyloxyethyl)-2-(3,4-dichloro benzene)acetonitrile 16.5 g of an 80% dispersion of sodium hydride in oil are suspended in 200 ml of dry tetrahydrofuran. A solution of 100 g of 3,4-dichlorophenylacetonitrile in 500 ml of tetrahydrofuran is added dropwise at 20° C. over 30 minutes and the reaction mixture is then stirred at room temperature for 2 hours. The mixture is cooled to −20° C., a solution of 118 g of 1-bromo-2-tetrahydropyranyloxyethane in 100 ml of tetrahydrofuran is added, the mixture is left to return to room temperature and, after 2 hours, a solution of 50 g of ammonium chloride in 3 liters of water is added. Extraction is carried out with 1.5 liters of ether and the extract is washed with a saturated solution of NaCl, decanted, dried over $MgSO_4$ and concentrated under vacuum. The residue is chromatographed on silica gel using $CH_2Cl_2$ and then ethyl acetate (95/5 v/v) as the eluent. The pure product fractions are concentrated under vacuum to give 118 g of an oil.

(b) 2-(2-Tetrahydropyranyloxyethyl)-2-(3,4-dichloro benzene)ethanamine 118 g of the nitrile obtained above are dissolved in 700 ml of absolute ethanol. 300 ml of concentrated aqueous ammonia are added, after which Raney nickel (10% of the amount of starting nitrile) is added while sweeping with nitrogen. Hydrogenation is then carried out under a hydrogen atmosphere at room temperature and ordinary pressure.

16 liters are absorbed in 4 hours. The catalyst is filtered off on Célite, the filtrate is concentrated under vacuum and the residue is taken up in a saturated solution of NaCl. After extraction with ether and drying over $MgSO_4$, 112 g of an oil are obtained.

(c) 2-(2-Hydroxyethyl)-2-(3,4-dichlorobenzene)ethanamine 81 g of the product obtained above according to (b) are dissolved in 38 ml of methanol. 80 ml of a solution of ethyl ether saturated with hydrochloric acid are added, the temperature being maintained at between 20° and 25° C. The mixture is stirred for 30 minutes at room temperature and then concentrated to dryness. The residue is dissolved in 250 ml of water, washed twice with ethyl ether, rendered alkaline with a solution of NaOH and extracted with $CH_2Cl_2$. After drying over $MgSO_4$, the extract is concentrated to dryness under vacuum, the residue is taken up in 800 ml of isopropyl ether, an insoluble material is filtered off on Célite, the filtrate is concentrated under vacuum to about 300 ml and seeded with crystals of aminoalcohol and the mixture is stirred overnight. The crystals are filtered off and rinsed with isopropyl ether and then with n-pentane to give 30.2 g of the expected product. M.p.=90°–91° C.

(d) 2-(2-Hydroxyethyl)-2-(3,4-dichlorobenzene)ethanamine (+)

A solution of 44.7 g of the product obtained according to step (c) above in 300 ml of methanol is added to a boiling solution of 29 g of D(−)-tartaric acid in 800 ml of methanol. The mixture is left to return to room temperature and stirred for 4 hours. The product is filtered off and rinsed with ethanol and then with ether to give 34.1 g of tartrate. This is recrystallized from 1.75 l of methanol to give 26.6 g of tartrate.

$[\alpha]_D^{25}=-4.2°$ (c=1, in $H_2O$)

This tartrate is taken up in 120 ml of water, rendered alkaline with a solution of NaOH and extracted twice with $CH_2Cl_2$ and the extract is dried over $MgSO_4$ and concentrated to dryness under vacuum. The residue is taken up in a small quantity of isopropyl ether, n-pentane is added and the mixture is filtered to give 15.4 g of the expected product. M.p.=79°–80° C.

$[\alpha]_D^{25}=+9.4°$ (c=1, in $CH_3OH$)

(e) N-Methyl-2-(2-hydroxyethyl)-2-(3,4-dichlorobenzene)ethanamine (+) hydrochloride

(e1) Ethyl N-[4-hydroxy-2-(3,4-di-chlorophenyl)butyl]carbamate 15 g of the product obtained according to step (d) above are dissolved in 200 ml of $CH_2Cl_2$. 9.9 ml of triethylamine are added. The mixture is cooled to 0° C. and a solution of 6.3 ml of ethyl chloroformate in 30 ml of $CH_2Cl_2$ is added dropwise at this temperature. After 15 minutes, the mixture is washed with water, then with a dilute solution of HCl and then with a saturated aqueous solution of $NaHCO_3$. After drying over $MgSO_4$, it is concentrated to dryness under vacuum to give 20 g of product in the form of an oil.

(e2) Reduction of the ethoxycarbonyl group to a methyl group

A solution of 20 g of the product obtained according to step (e1) above in 150 ml of anhydrous THF is added to 5.1 g of a suspension of lithium aluminum hydride in 60 ml of anhydrous THF. The mixture is refluxed for 1 hour. It is hydrolyzed with 20 ml of water, the inorganic material is filtered off and the filtrate is concentrated to dryness under vacuum. The oil obtained is dissolved in 100 ml of acetone. Ethyl ether saturated with hydrochloric acid is added to pH=1, after which ethyl ether is added until turbidity appears. The mixture is stirred for 1 hour and the crystals are filtered off and rinsed with a small quantity of acetone and then with ethyl ether to give 11 g of N-methyl-2-(2-hydroxyethyl)-2-(3,4-dichlorobenzene)ethanamine hydrochloride. M.p.=129° C.

$[\alpha]_D^{25}=+8.4°$ (c=1, in $CH_3OH$)

(f) N-Methyl-2-(2-hydroxyethyl)-2-(3,4-dichlorobenzene)ethanamine (−) hydrochloride The (−) enantiomer is obtained by following the above procedure and starting from L(+)-tartaric acid. M.p.=129° C.

$[\alpha]_D^{20}=-8.4°$ (c=1, in $CH_3OH$)

B. PHENYLACETIC ACIDS

PREPARATION II.1. 3-ISOPROPOXYPHENYLACETIC ACID

3-Isopropoxyphenylacetic acid is not known in the literature but can be prepared by well-known methods of preparing alkoxyphenylacetic acids.

(a) Ethyl 3-hydroxyphenylacetate

A solution of 55 g of 3-hydroxyphenylacetic acid in 400 ml of 100° ethanol is refluxed overnight in the presence of a few drops of concentrated $H_2SO_4$. It is evaporated to dryness under vacuum and the residue is taken up in ethyl ether and washed with water and then with a saturated aqueous solution of $NaHCO_3$. After drying over $MgSO_4$ followed by evaporation, 58 g of an oil are obtained.

(b) Ethyl 3-isopropoxyphenylacetate

A solution of 58 g of the product obtained above, 88 g of $K_2CO_3$ and 108 g of 2-iodopropane in 300 ml of DMF is heated at 80°–100° C. for 8 hours. The DMF is evaporated off under vacuum and the residue is taken up in ethyl acetate and washed with a 10% aqueous solution of $K_2CO_3$. After drying over $MgSO_4$ followed by evaporation, the residue is purified by chromatography on silica gel using $CH_2Cl_2$ as the eluent. This gives 61 g of an oil.

(c) 3-Isopropoxyphenylacetic acid

A solution of 31 g of the product obtained above and 20 g of NaOH in 400 ml of ethanol is refluxed for 2 hours. It is evaporated to dryness and the residue is taken up in water and acidified with concentrated HCl. Extraction is carried out with ethyl ether and the extract is washed with water, dried over $MgSO_4$ and concentrated to dryness under vacuum to give 27 g of the expected acid. M.p.=33°–35° C.

3-Ethoxyphenylacetic acid is prepared in the same way.

PREPARATION II.2. (3-ISOPROPOXYPHENYL) HYDROXYACETIC ACID

(a) 3-Isopropoxybenzaldehyde 50 g of 3-hydroxybenzaldehyde are dissolved, under nitrogen, in 250 ml of DMF. 60 g of $K_2CO_3$ and then 60 ml of 2-iodopropane are added and the reaction mixture is heated for 18 hours at 50° C. and poured into 2.5 liters of water. Extraction is carried out with ethyl ether and the ether phase is washed with a dilute solution of NaOH, dried over $MgSO_4$ and concentrated under vacuum to give 53.5 g of an oil.

(b) (3-Isopropoxyphenyl)hydroxyacetonitrile 0.72 g of sodium bisulfite is added to a suspension of 1 g of the product prepared above in 3 ml of water. The mixture is left for 18 hours at room temperature, a solution of 0.85 g of KCN in 2 ml of water is then added and the reaction mixture is stirred for 30 minutes. Extraction is carried out with ethyl ether and the extract is washed with water, dried over $Na_2SO_4$ and concentrated under vacuum to give 1.2 g of the expected compound in the form of an oil.

(c) (3-Isopropoxyphenyl)hydroxyacetic acid

A mixture of 1 g of the product obtained above in 1.1 ml of water and 1.1 ml of concentrated HCl is refluxed for one hour. The solution is left to cool and extracted with ethyl ether and the ether phase is washed with water and extracted with a dilute solution of NaOH. The aqueous phase is acidified with HCl and then extracted with ethyl ether and the extract is dried over $MgSO_4$ and concentrated under vacuum. The acid is crystallized from an isopropyl ether/pentane mixture (50/50) to give 0.42 g of the expected product; m.p.=94° C.

C. ACYL DERIVATIVES AND SULFONYLOXY DERIVATIVES PREPARATION III

1. Acylation via the acid 2-(2-Hydroxyethyl)-2-(3,4-dichlorophenyl)-N-(3-isopropoxyphenyl)-N-methylacetamide 6.05 ml of triethylamine and then 5.05 g of N-methyl-2-(2-hydroxyethyl)-2-(3,4-dichlorobenzene)ethanamine, prepared according to EP-A-474561, and 7.08 g of BOP are added to a solution of 2.8 g of 3-isopropoxyphenylacetic acid in 50 ml of $CH_2Cl_2$. After stirring for 4 hours at room temperature, the mixture is concentrated under vacuum and the residue is taken up in ethyl acetate and washed successively with water, with a dilute solution of NaOH and with a saturated solution of NaCl. The organic phase is dried over $MgSO_4$, filtered and concentrated under vacuum and the residue is chromatographed on silica gel using $CH_2Cl_2$/AcOEt (96/4 v/v) as the eluent. Concentration of the pure product fractions gives 7.0 g of the expected acylated compound.

2. Acylation via the acid chloride 2-(2-Hydroxyethyl)-2-(3,4-dichlorophenyl)-N-methylthiophene-2-carboxamide (−)

8.4 ml of triethylamine are added to a suspension of 8.1 g of the product obtained according to PREPARATION I (e) above in 120 ml of methylene chloride. The mixture is cooled to 0° C. and a solution of 2.97 g of 2-thenoyl chloride in 35 ml of methylene chloride is added dropwise. After 15 minutes, the mixture is washed with water, with a dilute solution of HCl and then with an aqueous solution of $NaHCO_3$. It is dried over $MgSO_4$, filtered and concentrated to dryness under vacuum to give 9.0 g of a solid, which is taken up in ethyl ether and filtered off. M.p.=107°–108° C.

$[\alpha]_D^{20}=-47.2°$ (C=1, $CH_3OH$)

PREPARATION IV

1. N-[4-(2-Methanesulfonyloxy)-2-(3,4-dichlorophenyl)butyl]-N-methyl-3-isopropoxyphenylacetamide 11.7 g of the product prepared above according to PREPARATION III 1. are dissolved in 100 ml of $CH_2Cl_2$ in the presence of 6.68 g of triethylamine, and 6.94 g of methanesulfonyl chloride are then added dropwise. The reaction mixture is left overnight at room temperature and then concentrated under vacuum. The residue is taken up in ethyl acetate and washed successively with water and with a saturated solution of NaCl and the organic phase is decanted, dried over $MgSO_4$, filtered and concentrated under vacuum. The residual oil is concentrated on silica gel using $CH_2Cl_2/CH_3OH$ (99/3 v/v) as the eluent. Concentration of the pure product fractions gives 11.04 g of the expected mesylate.

2. N-Methyl-N-[4-(2-methanesulfonyloxy)-2-(3,4-dichlorophenyl)butyl]thiophene-2-carboxamide (−)

4.8 ml of triethylamine are added to a solution of 10.71 g of the product obtained according to PREPARATION III 2. above in 120 ml of methylene chloride. The mixture is cooled to 0° C. and 2.7 ml of methanesulfonyl chloride are added dropwise. After 15 minutes, the mixture is washed twice with water and then with a saturated aqueous solution of NaCl. It is dried over $MgSO_4$, filtered and concentrated to dryness under vacuum to give a foam.

D. AMINE DERIVATIVES PREPARATION V

1. N-[4-(4-Phenylpiperidin-1-yl)-2-(3,4-dichlorophenyl)butyl]-N-methyl-3-isopropoxyphenylacetamide hydrochloride 2 g of the compound obtained according to PREPARATION IV 1. and 1.41 g of 4-phenylpiperidine are dissolved in 10 ml of DMF and the reaction mixture is heated at 70° C. for 3 hours. The solution is concentrated under vacuum, the residue is taken up in AcOEt and washed successively with water and with a saturated solution of NaCl and the organic phase is decanted, dried over MgSO$_4$, filtered and concentrated under vacuum. The residue is chromatographed on silica gel using CH$_2$Cl$_2$/CH$_3$OH (97/3 v/v) as the eluent. The pure product fractions are concentrated under vacuum, the base thus obtained in the form of an oil is then dissolved in ethyl ether, and gaseous hydrochloric acid is bubbled into the solution in order to prepare the hydrochloride of the base. 0.27 g of the expected product is obtained. M.p.=89°–91° C.

2. N-[4-(4-Hydroxy-4-phenylpiperidin-1-yl)-2-(3,4-dichlorophenyl)butyl]-N-methylthiophene-2-carboxamide (−)

12.12 g of the product obtained according to PREPARATION IV 2. above and 11.8 g of 4-hydroxy-4-phenylpiperidine are dissolved in 30 ml of DMF and heated at 70° C. for one and a half hours. The solution is poured into 30 ml of iced water and a precipitate is filtered off and dried. The precipitate obtained is purified by chromatography on silica gel using CH$_2$Cl$_2$/CH$_3$OH (90/10 v/v) as the eluent. The pure product fractions are concentrated under vacuum and the residue is then crystallized from ether. M.p.=120°14 121° C.

The hydrochloride is prepared in acetone by the addition of a solution of ethyl ether saturated with hydrochloric acid to pH=1. The precipitate is filtered off and dried.

$[\alpha]_D^{20}=-51.0°$ (c=1, CH$_3$OH)

3. N-[4-(4-Hydroxy-4-phenylpiperidin-1-yl)-2-(3,4-dichlorophenyl)butyl]-N-methyl-4-fluoro-1-naphthylamide hydrochloride 1.5 g of N-methyl-N-[4-(2-methanesulfonyloxy)-2-(3,4-dichlorophenyl)butyl]-4-fluoro-1-naphthylamide and 1.28 g of 4-hydroxy-4-phenylpiperidine are heated at 80°–90° C. in 8 ml of DMF for 3 hours. The reaction mixture is left to return to room temperature and then poured into water, extraction is carried out with ethyl acetate and the organic phase is washed successively with water and with a saturated solution of NaCl. The organic phase is then dried over MgSO$_4$, filtered and concentrated under vacuum. The residual oil is chromatographed on silica gel H using CH$_2$Cl$_2$/CH$_3$OH (98/2 v/v) as the eluent. The hydrochloride of the pure product fractions is prepared and then recrystallized from a mixture of acetone and ethyl acetate to give 2.1 g of the expected product. M.p.=180° C.

4. N-[4-(4-Benzylpiperidin-1-yl)-2-(3,4-dichlorophenyl)butyl]-N-methyl-3-ethoxy-1-phenylacetamide hydrochloride 2 ml of triethylamine and then 2.2 g of BOP are added to a solution of 2 g of N-(4-benzylpiperidin-1-yl)-2-(3,4-dichlorophenyl)-N-methylbutylamine and 0.8 g of 3-ethoxyphenylacetic acid in 40 ml of CH$_2$Cl$_2$. The reaction mixture is left for one hour at room temperature and then concentrated under vacuum. The residue is taken up in ethyl acetate and washed successively with water, with a dilute solution of NaOH and with a saturated solution of NaCl. The organic phase is dried over MgSO$_4$, filtered and concentrated under vacuum. The residue is purified by chromatography on silica gel using CH$_2$Cl$_2$/CH$_3$OH (100+1.7 v/v) as the eluent. The hydrochloride of the pure product fractions is prepared and 1.65 g of the expected hydrochloride are obtained. M.p.=130° C.

5. N-[4-(4-Benzylpiperidin-1-yl)-2-(3,4-dichlorophenyl)butyl]-N-methyl-3,5-dimethoxyphenylacetamide hydrochloride The expected product is obtained by following the above procedure according to PREPARATION V 4. and using 3,5-dimethoxyphenylacetic acid, prepared according to Tetrahedron Letters, 1991, 32, 23, 2663–2666. M.p.=150° C.

The compounds of formula (Ia) which are non-quaternary precursors of the compounds (I) according to the invention, listed in Table A below, were prepared using the PREPARATIONS indicated above.

TABLE A

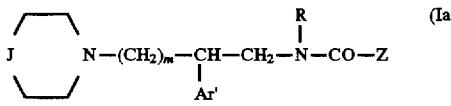

| J–N | m | Ar' | R | Z | F; °C. |
|---|---|---|---|---|---|
|  | 3 | 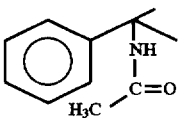 | CH$_3$ | 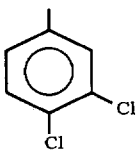 | 121 |
| 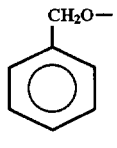 | 2 | 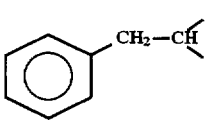 | CH$_3$ | 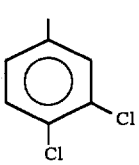 | 123 |

TABLE A-continued $$J\diagup\diagdown N-(CH_2)_m-CH(Ar')-CH_2-N(R)-CO-Z \quad (Ia)$$

| J\N (group) | m | Ar' | R | Z | F; °C. |
|---|---|---|---|---|---|
| PhCH₂-C(CH₃)(CH₂OH)- (piperidine) | 2 | 3,4-diClC₆H₃ | CH₃ | 3-(O-iPr)C₆H₄-CH₂- | 134 |
| PhCH(CH₃)- (piperidine) | 2 | 3,4-diClC₆H₃ | CH₃ | 4-F-1-naphthyl | énantiomère (−) 140 |
| PhCH₂-CH(CH₃)- (piperidine) | 3 | 1-naphthyl | H | 2,4-diOMe-C₆H₃ | 121 |
| PhCH₂-CH(CH₃)- (piperidine) | 2 | 1-naphthyl | H | 2,4,6-triOMe-C₆H₂ | 132 |
| PhCH₂-CH(CH₃)- (piperidine) | 2 | 1-methylindole-3-yl | H | 2,4-diOMe-C₆H₃ | 124 |

EXAMPLE 1

(Compound 1)

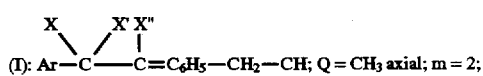

(I): Ar—C——C=C₆H₅—CH₂—CH; Q = CH₃ axial; m = 2;

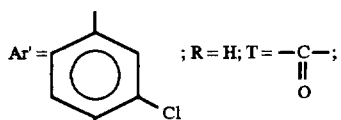  ; R = H; T = —C(=O)—;

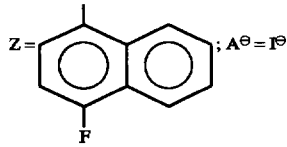  ; A⊖ = I⊖

2 g of N-[4-(4-benzylpiperidin-1-yl)-2-(3,4-dichlorophenyl)butyl]-4-fluoro-1-naphthylamide, prepared as indicated above according to EP-A-428434, are dissolved in 20 ml of methyl iodide. The solution is stirred at room temperature for 24 hours and then concentrated under vacuum. The residue is chromatographed on silica gel using CH₂Cl₂/CH₃OH (97/3 v/v) and then CH₂Cl₂/CH₃OH (95/5 v/v) as the eluent. The product eluted first corresponds to that in which the methyl in the 1-position on the nitrogen of the piperidine is in the axial position. The corresponding fraction is concentrated under vacuum to give 1.3 g of 1-[3-(3,4-dichlorophenyl)-4-(4-fluoro-1-naphthoylamino)butyl]-4-benzyl-N(a)-methyl-1-piperidinium iodide. M.p.= 120°–122° C.

¹H NMR: 7 H between 1.3 and 2.4 (2CH₂ and CH piperidine, CH₂β); 14 H between 2.45 and 3.9 (2CH₂N piperidine, CH₂ Ar, N⊕—CH₃, N⊕—CH₂, CH Ar', NH—CH₂); 14 H between 7 and 8.2 (all the aromatic H); 1 H at 8.5 (NH); DMSO at 2.49.

EXAMPLE 2

(Compound 2)

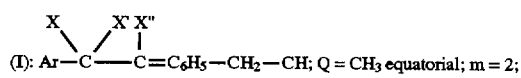

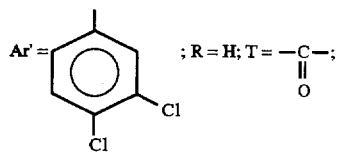

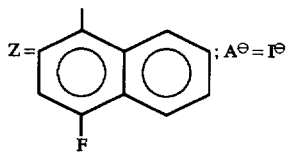

0.3 g of 1-[3-(3,4-dichlorophenyl)-4-(4-fluoro-naphthoylamino)butyl]-4-benzyl-N(e)-methyl-1-piperidinium iodide, in which the methyl in the 1-position on the nitrogen of the piperidine is in the equatorial position, is obtained by following the procedure described above in Example 1 and collecting the fraction eluted second. M.p.= 120°–122° C.

$^1$H NMR: 7 H between 1.3 and 2.4 (2CH$_2$ and CH piperidine, CH$_2$β); 14 H between 2.45 and 4 (2CH$_2$N piperidine, CH$_2$ Ar, N⊕—CH$_3$, N⊕—CH$_2$, CH Ar', CH$_2$—NH); 14 H between 7 and 8.3 (all the aromatic H); 1 H at 8.6 (NM); DMSO at 2.49.

EXAMPLE 3

(Compound 3)

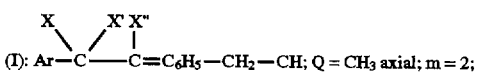

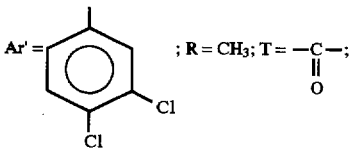

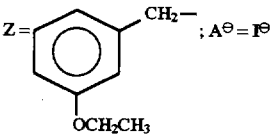

1-[3-(3,4-Dichlorophenyl)-4-(N-methyl-3-ethoxyphenyl-1-acetamido)butyl]-4-benzyl-N(a)-methyl-1-piperidinium iodide is prepared by following the procedure according to Example 1 and using N-[4-(4-benzylpiperidin-1-yl)-2-(3,4-dichlorophenyl)butyl]-N-methyl-3-ethoxy-1-phenylacetamide as the starting material. M.p.=90° C.

EXAMPLE 4

(Compound 4)

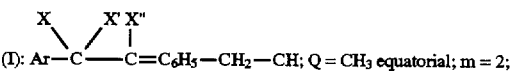

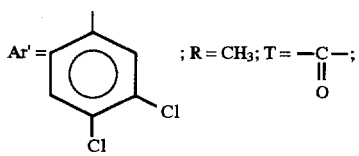

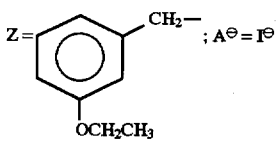

1-[3-(3,4-Dichlorophenyl)-4-(N-methyl-3-ethoxyphenyl-1-acetamido)butyl] -4-benzyl-N(e)-methyl-1-piperidinium iodide is prepared by following the procedure according to Example 2 and using N-[4-(4-benzylpiperidin-1-yl)-3-(3,4-dichlorophenyl)butyl]-N-methyl-3-ethoxy-1-phenylacetamide as the starting material. M.p.=105° C.

EXAMPLE 5

(Compound 5)

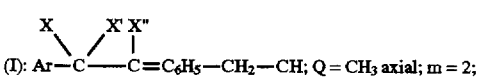

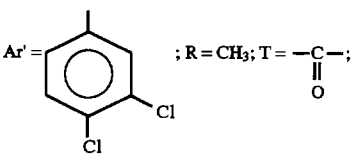

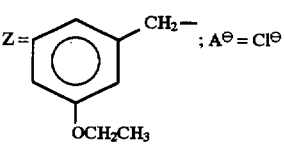

1 g of the iodide obtained according to Example (compound 3) is dissolved in 5 ml of 95° ethanol. 40 ml of Duolite A375® resin are conditioned in the chloride form and the solution prepared above is eluted on this column, which is then rinsed with 95° ethanol. The eluate is concentrated under vacuum and the residue is taken up in ether. The mixture is filtered to give 0.69 g of 1-[3-(3,4-dichlorophenyl)-4-(N-methyl-3-ethoxyphenyl-1-acetamido) butyl]-4-benzyl-N(a)-methyl-1-piperidinium chloride. M.p.=105° C.

EXAMPLE 6

(Compound 6)

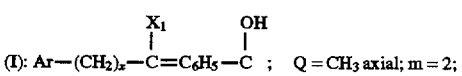

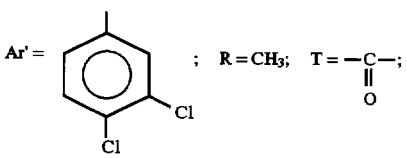

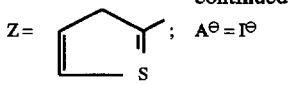

By following the above procedure according to Example 1, the piperidinium iodide of N-[4-(4-hydroxy-4-phenylpiperidin-1-yl)-2-(3,4-dichlorophenyl)butyl]-N-methylthiophene-2-carboxamide (−), described above according to PREPARATION V 2., is prepared by alkylation with methyl iodide. The compound in which the methyl is in the axial position on the nitrogen of the piperidine, namely 1-[3-(3,4-dichlorophenyl)-4-(N-methyl-2-thenoylamino)butyl]-4-hydroxy-4-Phenyl-N(a)-methyl-1-piperidinium (−) iodide, is eluted first. M.p.=150° C.

$[\alpha]_D^{20} = -44.9°$ (c=1, CH$_3$OH)

EXAMPLE 7

(Compound 7)

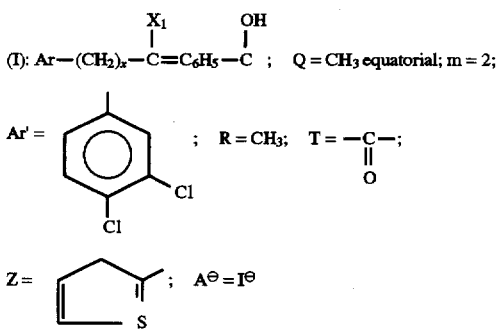

The quaternary salt of 1-[3-(3,4-dichlorophenyl)-4-(N-methyl-2-thenoylamino)butyl]-4-hydroxy-4-phenyl-N(e)-methyl-1-piperidinium (−) iodide, in which the methyl in the 1-position on the nitrogen of the piperidine is in the equatorial position, is obtained by following the procedure according to Example 6 and collecting the compound eluted second. M.p.=130° C.

$[\alpha]_D^{20} = -5.1°$ (c=1, CH$_3$OH)

EXAMPLE 8

(Compound 8)

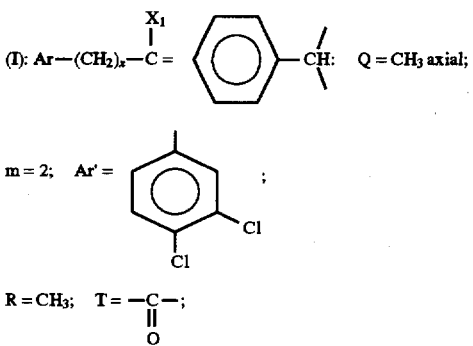

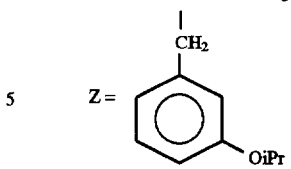

0.53 g of 1-[3-(3,4-dichlorophenyl)-4-(N-methyl-3-isopropoxyphenylacetylamino)butyl]-4-phenyl-N(a)-methyl-1-piperidinium iodide is obtained, as the first fraction eluted in chromatography, by following the procedure according to EXAMPLE 1 and reacting 1.1 g of N-[4-(4-phenylpiperidin-1-yl)-2-(3,4-dichlorophenyl)butyl]-N-methyl-3-isopropoxyphenylacetamide, prepared according to PREPARATION V 1., with 10 ml of methyl iodide. M.p.=105°–107° C.

$^{13}$C NMR: N⊕—CH$_3$: 33; N⊕—CH$_2$: 56.

EXAMPLE 9

(Compound 9)

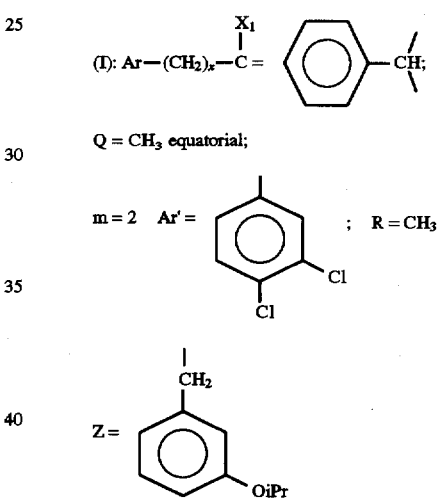

1-[3-(3,4-Dichlorophenyl)-4-(N-methyl-3-isopropoxyphenylacetylamino)butyl]-4-phenyl-N(e)-methyl-1-piperidinium iodide is obtained by following the procedure of EXAMPLE 8 and collecting the second fraction eluted in chromatography. M.p.=112°–114° C.

$^{13}$C NMR: N⊕—CH$_3$: 44; N⊕—CH$_2$: 46.

EXAMPLE 10

(Compound 10)

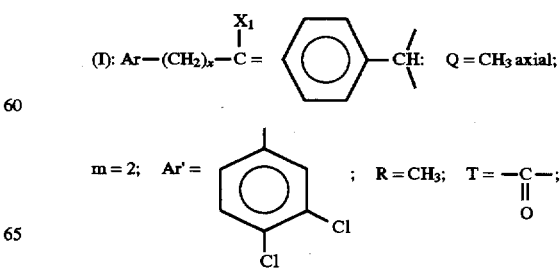

Z = 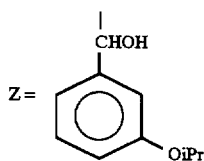

A) 6 g of ditert-butyl dicarbonate in 25 ml of AcOEt are added to a solution of 5.85 g of 2-(2-hydroxyethyl)-2-(3,4-dichlorobenzene)ethanamine, obtained according to PREPARATION I (c), in 150 ml of AcOEt and the mixture is left at room temperature for 20 minutes and then refluxed for 30 minutes. It is concentrated under vacuum to give 8.35 g of tertbutyl N-[4-hydroxy-2-(3,4-dichlorophenyl)butyl]carbamate.

B) 4 ml of triethylamine and 2.14 ml of mesyl chloride are added at −20° C. to a solution of 8.35 g of the carbamate obtained above in 100 ml of $CH_2Cl_2$. The reaction mixture is stirred at 0° C. for 2 hours and then extracted with diethyl ether. The ether phase is dried over $MgSO_4$, filtered and concentrated under vacuum to give 9.87 g of tert-butyl N-[4-methanesulfonyloxy-2-(3,4-dichlorophenyl)butyl]carbamate.

C) 9.87 g of the mesylate prepared above and 8.05 g of 4-phenylpiperidine are dissolved in 20 ml of DMF and the reaction mixture is heated at 60° C. for 2 hours. 100 ml of water are added and extraction is carried out with AcOEt. The organic phase is decanted and then successively dried over $Na_2SO_4$, filtered and concentrated under vacuum to give 11.8 g of tertbutyl N-[4-(4-phenylpiperidin-1-yl)-2-(3,4-dichlorophenyl)butyl]carbamate.

D) A solution of 11.8 g of the product prepared above in 30 ml of anhydrous THF is added to a suspension of 2.9 g of lithium aluminum hydride in 40 ml of anhydrous THF and the reaction mixture is refluxed for 2 hours. It is hydrolyzed by the addition of 15 ml of water, the inorganic material is filtered off and the filtrate is concentrated under vacuum. The residue is taken up in 20 ml of $CH_2Cl_2$ and 10 ml of a solution of diethyl ether saturated with HCl and the mixture is then concentrated under vacuum to give 6.7 g of N-[4-(4-phenylpiperidin-1-yl)-2-(3,4-dichlorophenyl)butyl]-N-methylamine, which crystallizes from acetone.

E) 3.17 ml of triethylamine, 1.40 g of (3-isopropoxyphenyl)hydroxyacetic acid, obtained according to PREPARATION II 2., and 3.14 g of BOP are added successively to a solution of 3 g of the amine prepared above in 60 ml of $CH_2Cl_2$. The reaction mixture is stirred at room temperature for one hour and then washed successively with water and with a solution of $NaHCO_3$. The organic phase is decanted, dried over $Na_2SO_4$, filtered and concentrated under vacuum. The residue is chromatographed on silica gel using $CH_2Cl_2/CH_3OH$ (97/3 v/v) as the eluent. Concentration of the pure product fractions gives an oily residue, to which a solution of diethyl ether saturated with HCl is added to give 2 g of N-[4-(4-phenylpiperidin-1-yl)-2-(3,4-dichlorophenyl)butyl]N-methyl-α-hydroxyphenylacetamide dihydrochloride.

F) Methyl iodide is reacted with the acetamide prepared above, under the same conditions as for the previous Examples, to give 1-[3-(3,4-dichlorophenyl)-4-(N-methyl-α-hydroxyphenylacetamido)butyl]-4-phenyl-N(a)-methyl-1-piperidinium iodide; m.p.=130° C.

EXAMPLE 11

(Compound 11)

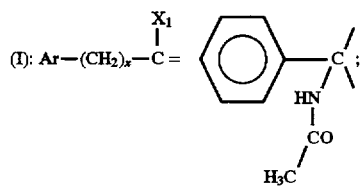

Q = $CH_3$ axial/equatorial; m = 3; Ar' = 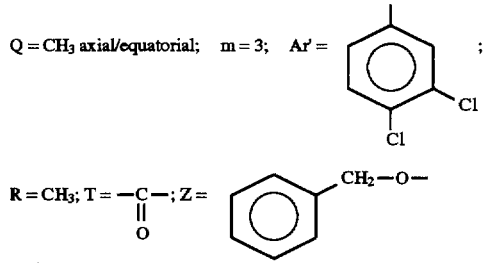

R = $CH_3$; T = —C—; Z =
            ||
            O

1-[4-(3,4-Dichlorophenyl)-5-(benzyl N-methylcarbamate)pentyl]-4-phenyl-4-acetylamino-N(a,e)-methyl-1-piperidinium iodide is obtained by reacting methyl iodide with benzyl N-methyl-N-[5-(4-acetylamino-4-phenylpiperidin-1-yl)-2-(3,4-dichlorophenyl)pentyl]-N-carbamate under the same conditions as for the previous EXAMPLES; m.p.=133° C.

Compounds 12 to 36 described in TABLES I and II below are prepared by following the procedure of the previous PREPARATIONS and of EXAMPLES 1 to 11 above.

TABLE I

Structure: J-N⁺(Q)(CH₂CH₂-ring)-(CH₂)₂-CH(3,4-dichlorophenyl)-N(R)-CH₂-CO-Z, I⁻ counterion

| Exemple n° | J | Q⁽¹⁾ | C⁽²⁾ | R | Z | F; °C. |
|---|---|---|---|---|---|---|
| 12 | PhCH₂-CH< | CH₃ (a) | (+, −) | CH₃ | 4-fluoro-1-naphthyl | 127 |
| 13 | PhCH₂-CH< | CH₃ (a) | −25, 6 | CH₃ | 4-fluoro-1-naphthyl | 158–160 |
| 14 | PhCH₂-CH< | CH₃ (a) | (+, −) | CH₃ | 3-(O-iPr)benzyl | 129–145 |
| 15 | PhCH₂-CH< | CH₃ (e) | (+, −) | CH₃ | 3-(O-iPr)benzyl | 136–155 |
| 16 | PhCH₂-CH< | CH₃ (a) | (+, −) | CH₃ | 3,5-dimethoxybenzyl | 100 |
| 17 | PhCH₂-CH< | CH₃ (e) | (+, −) | CH₃ | 3,5-dimethoxybenzyl | 115 |
| 18 | Ph-CH₂-C(OH)< | CH₃ (a) | (+, −) | CH₃ | 3-(O-iPr)benzyl | 125–127 |
| 19 | Ph-CH₂-C(OH)< | CH₃ (e) | (+, −) | CH₃ | 3-(O-iPr)benzyl | 162–164 |

TABLE I-continued

[Structure: J-N⁺(Q)(piperidine ring)-(CH₂)₂-CH(3,4-dichlorophenyl)-N(R)-CH₂-CO-Z, I⁻ counterion]

| Exemple n° | J | Q⁽¹⁾ | C⁽²⁾ | R | Z | F; °C. |
|---|---|---|---|---|---|---|
| 20 | PhCH< | CH₃ (a) | −35, 5 | CH₃ | 3-(O-iPr)-benzyl (CH₂-C₆H₄-O-iPr) | 101–103 |
| 21 | PhCH< | CH₃ (e) | −7, 6 | CH₃ | 3-(O-iPr)-benzyl | 105–107 |
| 22 | PhCH< | CH₃ (a) | −31, 9 | CH₃ | 4-fluoronaphthalen-1-yl | 162–164 |
| 23 | PhCH< | CH₃ (e) | +1, 9 | CH₃ | 4-fluoronaphthalen-1-yl | 154–156 |
| 24 | HO-C(Ph)< | CH₃ (a) | (+, −) | CH₃ | 4-fluoronaphthalen-1-yl | 157 |

⁽¹⁾: Configuration of the substituent Q: (a) = axial, (e) = equatorial;
⁽²⁾: Absolute configuration of the asymmetric carbon and α_D in ° at 25° C., C = 1 in CH₃OH.

TABLE II

[Structure: Ph-(CH₂)ₓ-(piperidine)-N⁺(Q)-(CH₂)ₘ-CH(Ar')-CH₂-NHCO-Z, I⁻ counterion]

| Exemple n° | x | Q⁽¹⁾ | m | Ar' | Z | F; °C. |
|---|---|---|---|---|---|---|
| 25 | 0 | CH₃ (a) | 2 | naphthalen-1-yl | 2,5-dimethoxyphenyl | 130–132 |

TABLE II-continued

| Exemple n° | x | Q(1) | m | Ar' | Z | F; °C. |
|---|---|---|---|---|---|---|
| 26 | 0 | CH₃ (e) | 2 | naphthyl | 2,4-dimethoxyphenyl | 125–127 |
| 27 | 1 | CH₃ (e) | 3 | naphthyl | 2,4-dimethoxyphenyl | 132 |
| 28 | 1 | CH₃ (a) | 3 | naphthyl | 2,4-dimethoxyphenyl | 123 |
| 29 | 1 | CH₃ (a) | 2 | naphthyl | 2,4-dimethoxyphenyl | 128–130 |
| 30 | 1 | CH₃ (e) | 2 | naphthyl | 2,4-dimethoxyphenyl | 116–118 |
| 31 | 1 | CH₃ (a) | 2 | naphthyl | 2,4,6-trimethoxyphenyl | 124 |
| 32 | 1 | CH₃ (e) | 2 | naphthyl | 2,4,6-trimethoxyphenyl | 143 |
| 33 | 1 | CH₃ (a) | 2 | N-methylindol-3-yl | 2,4-dimethoxyphenyl | 134 |
| 34 | 1 | CH₃ (e) | 2 | N-methylindol-3-yl | 2,4-dimethoxyphenyl | 138 |

TABLE II-continued

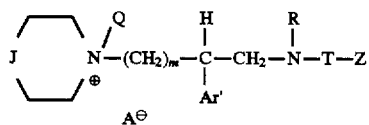

| Exemple n° | x | Q$^{(1)}$ | m | Ar' | Z | F; °C. |
|---|---|---|---|---|---|---|
| 35 | 1 | CH$_3$ (a) | 2 | indole (N-H) | 2,4-dimethoxyphenyl (OCH$_3$, OCH$_3$) | 135–140 |
| 36 | 1 | CH$_3$ (e) | 2 | indole (N-H) | 2,4-dimethoxyphenyl (OCH$_3$, OCH$_3$) | 98 |

$^{(1)}$: Configuration of the substituent Q: (a) = axial, (e) = equatorial.

What is claimed is:

1. A quaternary ammonium salt of the formula

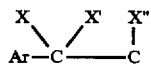

(I)

in which:

J is

\*—either a group

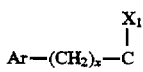

in which:

Ar is a phenyl which is unsubstituted or monosubstituted or polysubstituted by a substituent selected from: hydrogen, a halogen atom, a hydroxyl, a $C_1$–$C_3$-alkoxy, a $C_1$–$C_3$-alkyl and a trifluoromethyl, said substituents being identical or different; a $C_3$–$C_7$-cycloalkyl group; a pyridyl group; or a thienyl group;

X is hydrogen;

X' is hydrogen or is combined with X" below to form a carbon-carbon bond, or else X and X' together form an oxo group; and X" is hydrogen or forms a carbon-carbon bond with X';

\*—or a group

in which:

Ar is as defined above;

x is zero or one; and $X_1$ is hydrogen, only when x is zero; a hydroxyl; a $C_1$–$C_4$-alkoxy; a $C_1$–$C_4$-acyloxy; a carboxyl; a $C_1$–$C_4$-carbalkoxy; a cyano; a group —NH—CO—Alk in which Alk is a $C_1$–$C_6$-alkyl; a mercapto group; or a $C_1$–$C_6$-alkylthio group; or else $X_1$ forms a double bond with the carbon atom to which it is bonded and with the adjacent carbon atom in the piperidine;

Q is a $C_1$–$C_6$-alkyl group or a benzyl group;

A$\ominus$ is an anion selected from chloride, bromide, iodide, acetate, methanesulfonate and paratoluenesulfonate;

m is 2 or 3;

Ar' is a phenyl which is unsubstituted or monosubstituted or polysubstituted by a substituent selected from: hydrogen, a halogen atom, preferably a chlorine or fluorine atom, a trifluoromethyl, a $C_1$–$C_4$-alkoxy and a $C_1$–$C_4$-alkyl, said substituents being identical or different; a thienyl; a benzothienyl; naphthyl; or an indolyl optionally N-substituted by a $C_1$–$C_4$-alkyl;

R is hydrogen or a $C_1$–$C_6$-alkyl;

T is a group selected from:

$$-\underset{\parallel}{\underset{O}{C}}-\quad \text{and} \quad -\underset{\parallel}{\underset{W}{C}}-NH-,$$

W being an oxygen or sulfur atom; and

Z is hydrogen, M or OM when T is the group $$-\underset{\parallel}{\underset{O}{C}}-,$$

or M when T is the group $$-\underset{\parallel}{\underset{W}{C}}-NH-,$$

M being a $C_1$–$C_6$-alkyl ; an α-hydroxybenzyl, an α-hydroxybenzylalkyl or phenylalkyl in which the alkyl is $C_1$–$C_3$ and which is unsubstituted or monosubstituted or polysubstituted on the aromatic ring by a halogen, a trifluoromethyl, a $C_1$–$C_4$-alkyl, a hydroxyl or a $C_1$–$C_4$-alkoxy; a pyridylalkyl in which the alkyl is $C_1$–$C_3$; a naphtylalkyl in which the alkyl is $C_1$–$C_3$ and which is unsubstituted or substituted on the naphthyl ring by a halogen, a trifluoromethyl, a $C_1$–$C_4$-alkyl, a hydroxyl or a $C_1$–$C_4$-alkoxy; a pyridylthioalkyl in which the alkyl is $C_1$–$C_3$; a styryl; or a subsituted or unsubstituted mono-, di or tri-cyclic aromatic or heteroaromatic group.

2. A compound according to claim 1 of formula (I) in which Z is naphthyl, benzyl, α-hydroxybenzyl or phenyl which are unsubstituted or substituted by a substituent selected from chlorine or fluorine and $C_1$–$C_4$-alkyl or -alkoxy.

3. A compound according to claim 2 of formula (I) in which R is hydrogen or methyl, Ar' is 3,4-dichlorophenyl, and T is carbonyl.

4. 1-[3-(3,4-Dichlorophenyl)-4-(N-methyl-3-isopropoxyphenylacetylamino)butyl]-4-phenyl-N(a)-methyl-1-piperidinium iodide, a compound according to claim 1.

5. 1-[3-(3,4-Dichlorophenyl)-4-(N-methyl-3-isopropoxyphenylacetylamino)butyl]-4-phenyl-N(e)-methyl-1-piperidinium iodide, a compound according to claim 1.

6. 1-[3-(3,4-Dichlorophenyl)-4-(N-methyl-α-hydroxyphenylacetamido)butyl]-4-phenyl-N(a)-methyl-1-piperidinium iodide, a compound according to claim 1.

7. A pharmaceutical composition which comprises a compound according to claim 1, and a pharmaceutically acceptable excipient.

8. A pharmaceutical composition according to claim 7 in the form of a dosage unit.

* * * * *